(12) United States Patent
Smith et al.

(10) Patent No.: US 10,738,810 B2
(45) Date of Patent: Aug. 11, 2020

(54) TROCAR PACKAGING CLIP

(71) Applicant: Covidien LP, Mansfield, MA (US)

(72) Inventors: Samantha Smith, Shelton, CT (US);
Krishnakumar Somasundaram, New Haven, CT (US); Rahul Shinde, Karnataka (IN); Roshan Lohar, Karnataka (IN); Richard C. Hart, Clinton, CT (US)

(73) Assignee: Covidien LP, Mansfield, MA (US)

( * ) Notice: Subject to any disclaimer, the term of this patent is extended or adjusted under 35 U.S.C. 154(b) by 723 days.

(21) Appl. No.: 14/724,101

(22) Filed: May 28, 2015

(65) Prior Publication Data

US 2015/0351844 A1    Dec. 10, 2015

Related U.S. Application Data

(60) Provisional application No. 62/007,572, filed on Jun. 4, 2014.

(51) Int. Cl.
*F16B 2/22* (2006.01)
*A61B 17/34* (2006.01)
*A61B 50/20* (2016.01)
*A61B 50/30* (2016.01)

(52) U.S. Cl.
CPC ............... *F16B 2/22* (2013.01); *A61B 17/34* (2013.01); *A61B 17/3421* (2013.01); *A61B 50/20* (2016.02); *A61B 50/30* (2016.02); *A61B 17/3478* (2013.01); *A61B 17/3498* (2013.01); *Y10T 24/4465* (2015.01)

(58) Field of Classification Search
CPC ....... Y10T 24/4465; F16B 2/22; A61B 50/30; A61B 2050/3009; A61B 17/3478; A61B 17/3498; A61B 2017/00362
See application file for complete search history.

(56) References Cited

U.S. PATENT DOCUMENTS

| | | |
|---|---|---|
| 4,711,636 A | 12/1987 | Bierman |
| 5,290,259 A | 3/1994 | Fischer |
| 5,833,667 A | 11/1998 | Bierman |
| 6,074,368 A | 6/2000 | Wright |
| 6,610,033 B1 | 8/2003 | Melanson et al. |
| 6,936,033 B2 | 8/2005 | McIntosh et al. |
| 7,678,083 B2 | 3/2010 | Stephens |
| 7,785,312 B2 | 8/2010 | Thorne, Jr. et al. |
| 7,918,828 B2 | 4/2011 | Lundgaard et al. |
| 2005/0067308 A1 * | 3/2005 | Thompson ............. A61B 17/34 206/363 |

FOREIGN PATENT DOCUMENTS

EP        0790063 A1 *  8/1997  ............ A61M 5/002

* cited by examiner

*Primary Examiner* — Nathan R Price
*Assistant Examiner* — Justin L Zamory
(74) *Attorney, Agent, or Firm* — Carter, DeLuca & Farrell LLP

(57) ABSTRACT

A packaging device for a trocar assembly includes a trocar packaging clip having at least two holding structures configured to be detachably secured to the proximal portions of the trocar obturator and the cannula for retention of the trocar obturator and cannula relative to each other. The trocar packaging clip includes an anti-rotation structure configured to engage at least one of the trocar and the cannula to prevent relative rotation thereof.

9 Claims, 5 Drawing Sheets

TROCAR PACKAGING CLIP

CROSS-REFERENCE TO RELATED APPLICATIONS

This application claims the benefit of and priority to U.S. Provisional Patent Application No. 62/007,572, filed Jun. 4, 2014, the entire disclosure of which is incorporated by reference herein.

BACKGROUND OF THE INVENTION

Technical Field

The present invention relates to packaging devices for trocar assemblies, and more particularly, to a trocar assembly packaging device that prevents a trocar cannula and an obturator from rotating.

Background of Related Art

Minimally invasive surgical procedures, including endoscopic, laparoscopic and arthroscopic procedures, have been used for introducing medical devices inside a patient and for viewing portions of the patient's anatomy. Forming a relatively small diameter, temporary pathway to the surgical site is a key feature of most minimally invasive surgical procedures. The most common method of providing such a pathway is by inserting a trocar assembly through the skin. Typically, and shown in FIGS. 1 and 2, a trocar assembly 1010 includes a trocar cannula 1000, having a cannula housing 1002 and a cannula sleeve 1004, and a trocar obturator 100, having an obturator housing 102 and an obturator shaft 104.

Obturators are typically designed with a tip that may be used to form an opening through the abdominal wall. The obturator is inserted into the trocar cannula, and then the combined obturator and trocar cannula are together placed against the skin to be penetrated. In order to penetrate the skin, the distal end of the obturator engages the skin, which may or may not have been previously cut with a scalpel. The trocar obturator is then used to penetrate the skin and access the body cavity. By applying pressure against the proximal end of the trocar obturator, the tip of the trocar obturator is forced though the skin and the underlying tissue layers until the cannula and obturator enter the body cavity. The obturator is then withdrawn. The cannula remains in place within the incision for use during the laparoscopic, endoscopic, or arthroscopic procedure.

Conventional packaging for surgical trocar assemblies may have various disadvantages. For example, even if the material used for the sterile barrier is typically strong, movement of the surgical devices within the packaging during storage or transportation may inadvertently puncture the packaging material. When the packaging material is punctured, the devices are no longer sterile and cannot be used by a surgeon in a surgical procedure.

As a result, it is readily apparent that a trocar assembly packaging device is needed which overcomes the shortcomings of prior art trocar assembly packaging arrangements, and specifically which helps prevent inadvertent puncture of the packaging material by the trocar assembly during storage and transportation.

SUMMARY OF THE INVENTION

The present invention, in accordance with various embodiments thereof, relates to a trocar assembly, comprising: a trocar obturator having a proximal portion; a cannula having a proximal portion; and a trocar packaging clip having at least two holding structures, wherein each holding structure is configured to be detachably secured to the proximal portions of the trocar obturator and the cannula for retention of the trocar obturator and cannula relative to each other. The trocar packaging clip may further comprise a finger configured to prevent the cannula from rotating. The finger may define a notch. The linger may further comprise two notch sides, the two notch sides defining the notch. The cannula may further comprise a valve having a lever, the notch configured to engage the lever and prevent relative rotation thereof.

At least one of the holding structures may define a c-shape configured to securely retain the trocar obturator or the cannula. At least one of the holding structures may define a gap into which the trocar obturator or the cannula can be pressed. At least one of the holding structures may be configured to open when the trocar obturator or cannula is inserted. The trocar packaging clip may further comprise at least one guard that is affixed to at least one of the holding structures adjacent to the outer perimeter of the trocar. The trocar assembly may further comprise a sterile package into which the trocar obturator, cannula and trocar packaging clip are sealed. In addition, the trocar assembly may further comprise a second cannula. The trocar packaging clip may be formed from plastic.

The present invention, in accordance with various embodiments thereof, also relates to a trocar assembly configured to be shipped in a packaging container, the trocar assembly comprising: a trocar obturator; a cannula; and a trocar packaging clip having at least two holding structures, wherein the holding structures are configured to be detachably secured to the trocar obturator and to the cannula for retention of the trocar obturator and cannula in a fixed position relative to each other; wherein the trocar packaging clip includes an anti-rotation structure configured to engage at least one of the trocar and the cannula to prevent relative rotation thereof. At least one of the holding structures may define a c-shape configured to securely retain the trocar obturator or the cannula. At least one of the holding structures may define a gap into which the trocar obturator or the cannula can be pressed. At least one of the holding structures may be configured to allow the trocar obturator or cannula to be inserted. The trocar packaging clip may further comprise at least one guard that is affixed to the packaging clip nearby the outer perimeter of the trocar. The trocar assembly may further comprise a sterile package into which the trocar obturator, cannula and trocar packaging clip are sealed. The anti-rotation structure may comprise a finger configured to prevent the cannula from rotating. The finger may define a notch. The finger may further comprise two notch sides, the two notch sides defining the notch. The cannula may further comprise a valve having a lever, the notch configured to engage the lever and prevent relative rotation thereof.

The present invention, in accordance with various embodiments thereof, may also relate to a trocar assembly including a packaging device, comprising: a trocar obturator; a cannula having a valve; and a clip configured to detachably secure the trocar obturator and the cannula relative to each other, the clip including a finger configured to engage the valve on the cannula to prevent relative rotation of the valve. The clip may include at least one holding structure that defines a c-shape. The clip may define a gap into which the trocar obturator or the cannula can be pressed. The clip may further comprise at least one holding structure configured to retain the trocar obturator or cannula. The clip may further comprise at least one guard. The finger may define a notch. The finger may further comprise two notch sides, the two notch sides defining the notch. The cannula may further comprise a valve having a lever, the notch configured to engage the lever and prevent relative rotation thereof.

BRIEF DESCRIPTION OF THE DRAWINGS

Various features of the present invention will become more readily apparent and will be better understood by referring to the following detailed description of the present invention, which are described hereinbelow with reference to the drawings wherein.

DETAILED DESCRIPTION OF THE EMBODIMENTS

Figure 1:
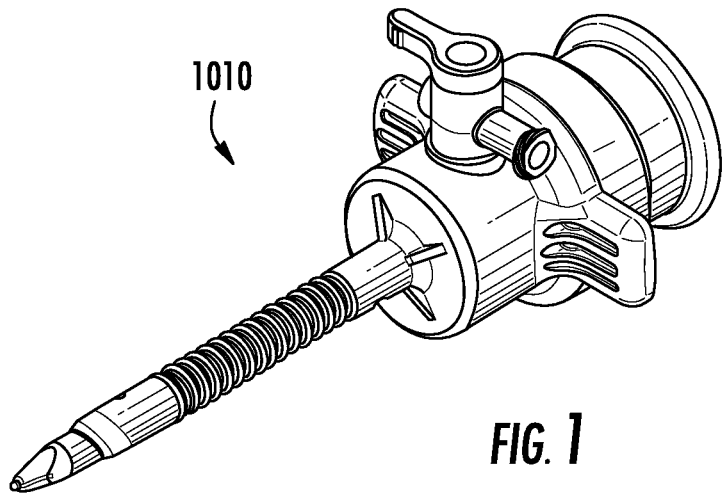
FIG. 1 is a perspective view of a conventional trocar cannula and obturator when assembled together in accordance with the prior art.
Figure 2:
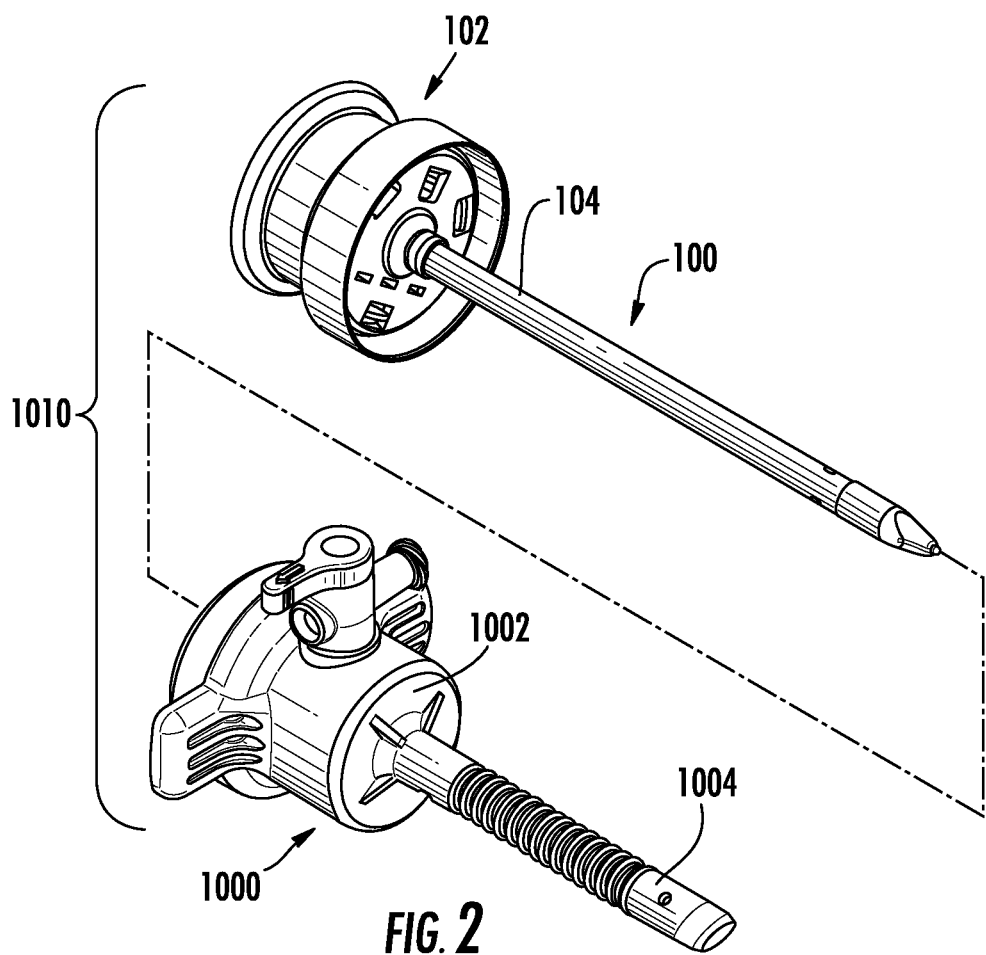
FIG. 2 is a perspective view of the cannula assembly and the obturator assembly of FIG. 1 when separated.
Figure 3:
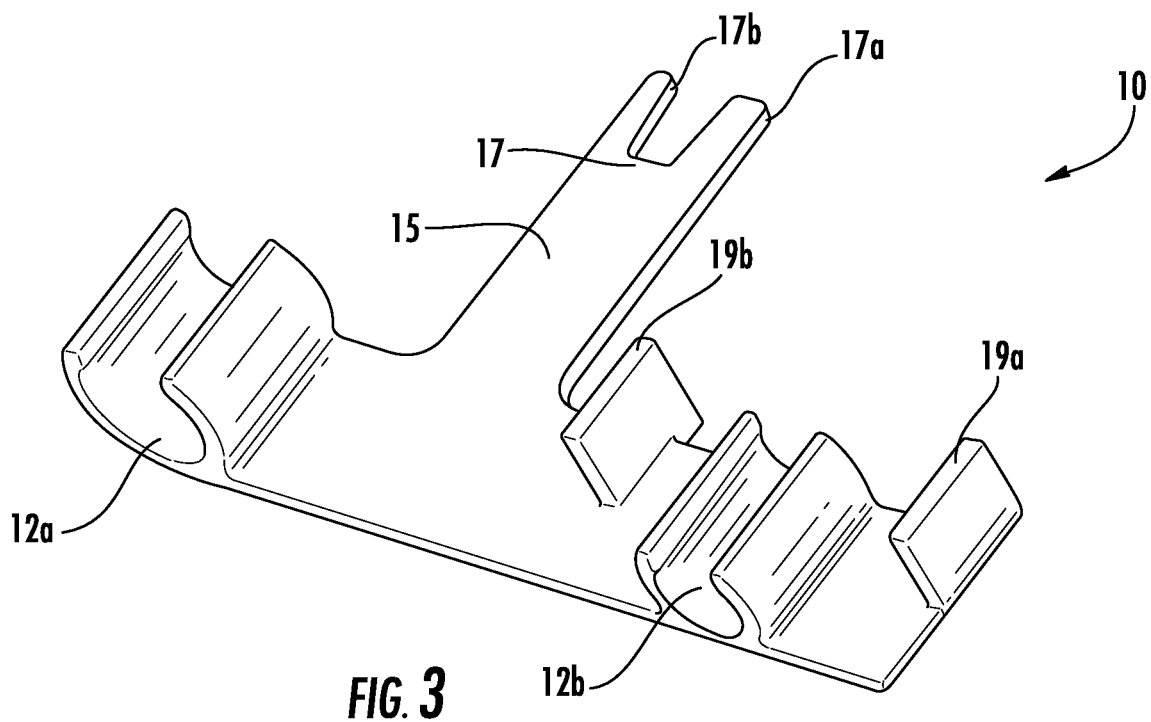
FIG. 3 is a front perspective view of a trocar packaging clip, in accordance with an embodiment of the present invention.
Figure 4:
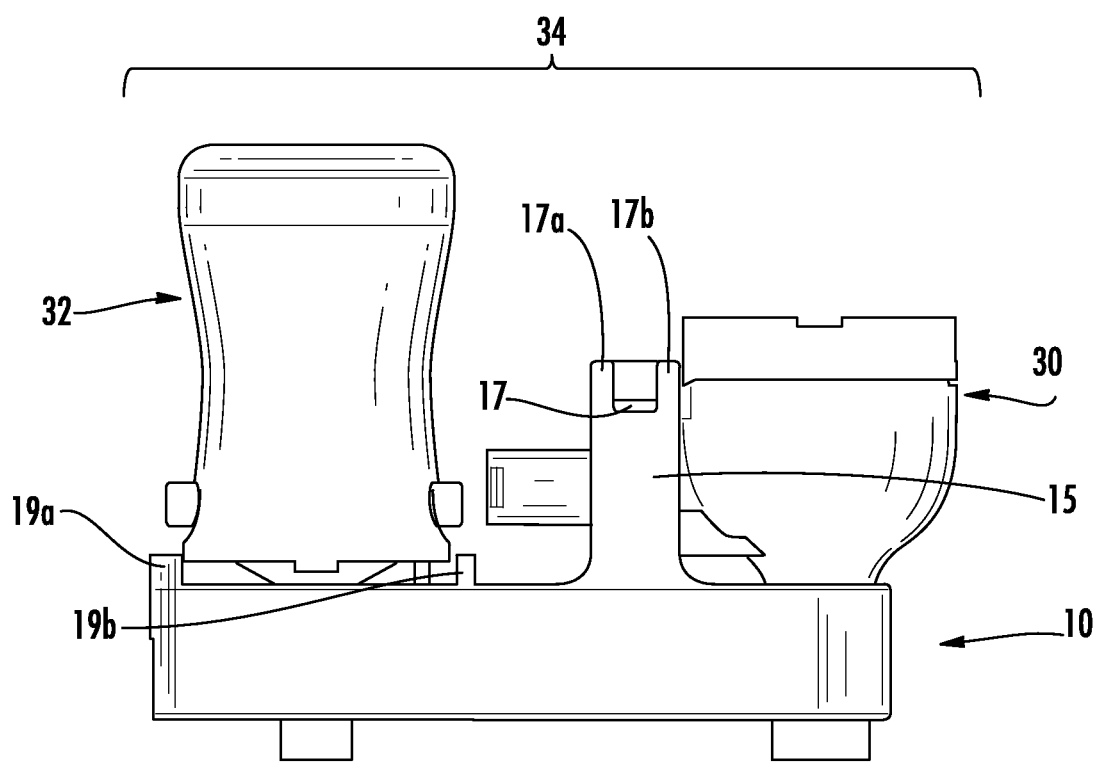
FIG. 4 is a rear view of the trocar packaging clip of FIG. 3 having a trocar cannula and trocar obturator attached thereto.
Figure 5:
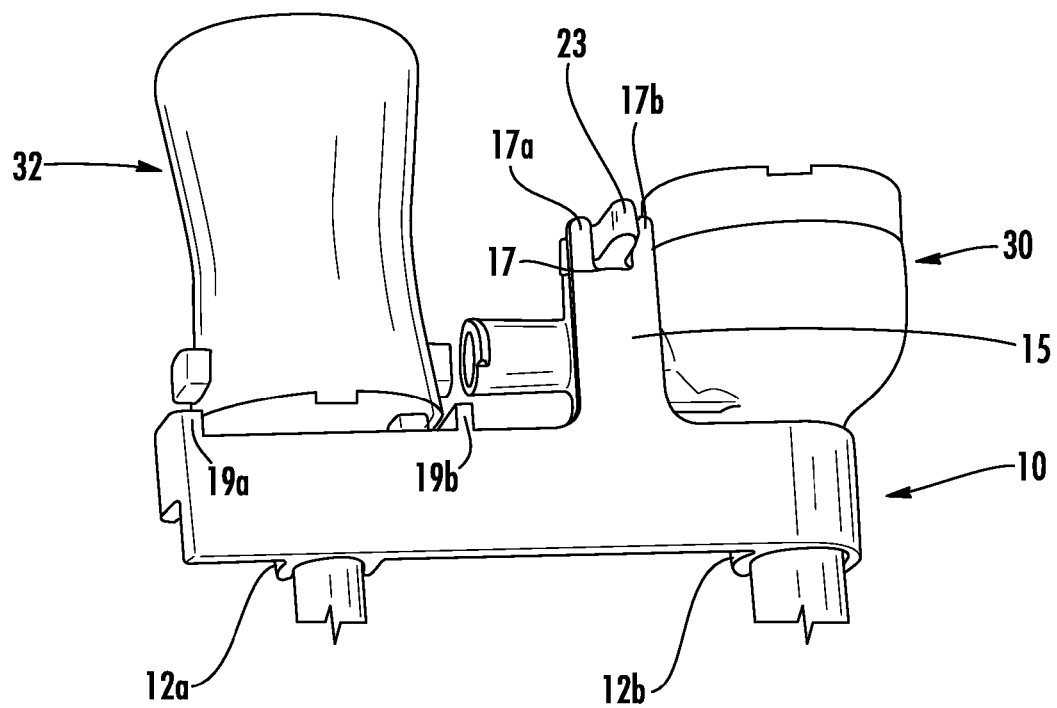
FIG. 5 is a rear perspective view of the trocar packaging clip of FIG. 3 having a trocar cannula and trocar obturator attached thereto.
Figure 6:
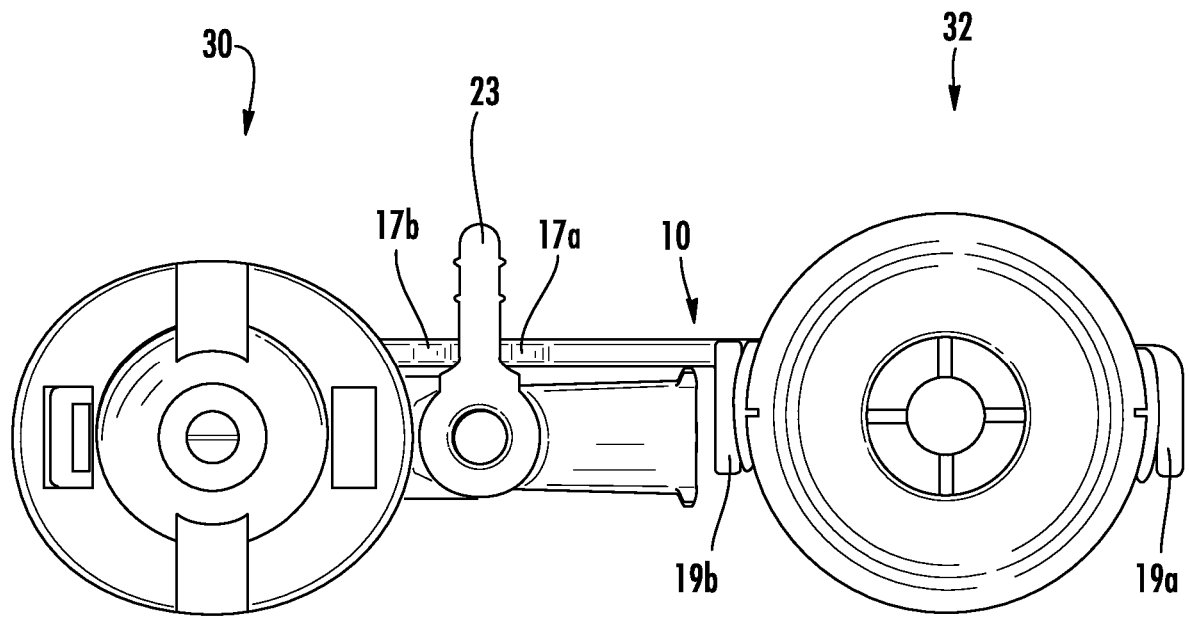
FIG. 6 is a top view of the trocar packaging clip of FIG. 3 having a trocar cannula and trocar obturator attached thereto.

The detailed description of the present invention is disclosed herein. The disclosed embodiments are merely exemplary of the invention, which may be embodied in various forms. The detailed disclosure herein should not be interpreted as limiting, but merely as the basis for the claims and as a basis tier teaching one skilled in the art how to make and/or used the invention.

With reference to FIGS. 3 to 6 there is disclosed, in accordance with various embodiments of the present invention, a packaging clip 10 for trocar assembly components, such as a trocar cannula 30 and a trocar obturator 32 of a trocar assembly 34.

The trocar packaging clip 10, in accordance with various embodiments, is particularly well-suited for use in conjunction with trocar assemblies of various sizes, including conventional trocar sizes such as 5 mm to 15 mm diameters and therebetween. The packaging clip 10 may be molded from a compliant material, for example, elastomer or plastic. While the present packaging device is disclosed in accordance with a preferred embodiment as being constructed from a particular material, those skilled in the art will appreciate that the packaging device may be manufactured from a variety of similar materials without departing from the spirit of the present invention.

The packaging clip 10, according to the embodiments shown in FIGS. 3 to 6, includes two holding structures 12a and 12b that are located apart from each other on the packaging clip 10 in a manner to secure the proximal portions of the trocar obturator 32 and the trocar cannula 30, respectively. The holding structures 12a and 12b can be formed integrally with the packaging clip 10, or may be affixed to the packaging clip 10 separately after the packaging clip 10 is formed. The holding structures 12a and 12b may define gaps into which the trocar obturator 32 and/or the trocar cannula 30 can be pressed. The holding structures 12a and 12b retain the trocar cannula 30 and trocar obturator 32 fixed relative to each other after they inserted in the holding structures 12a and 12b. Because the trocar cannula 30 is typically slightly larger in diameter that the trocar obturator 32 that passes therethrough, the holding structures 12a and 12b may have different diameters. In the present embodiment of the packaging clip 10 the holding structure 12a, for accommodating the trocar obturator 32, may be slightly smaller than the holding structure 12b, for accommodating the trocar cannula 30.

In various embodiments of the present invention, the holding structures 12a and 12b may define a c-shape (as shown) or may define other shapes, such as squares, triangles, or any other shape that is formed by the outer surface of the trocar obturator 32 or trocar cannula 30. In another embodiment, the holding structures 12a and 12b may be circular in shape and may be attached or affixed to the packaging clip 10 without defining an opening or gap. The trocar obturator 32 and the trocar cannula 30 in this embodiment may be inserted in holding structures 12a and 12b of the packaging clip 10 from the top. In another embodiment, the holding structures 12a and 12b may be devoid of an opening, but when the trocar cannula 30 and trocar obturator 32 are pressed against it, a prearranged part of the holding structure 12a or 12b is detached or removed, creating an opening, in order to facilitate the entrance of such devices and to secure the positioning of such devices in the holding structures 12a and 12b.

Figure 10:
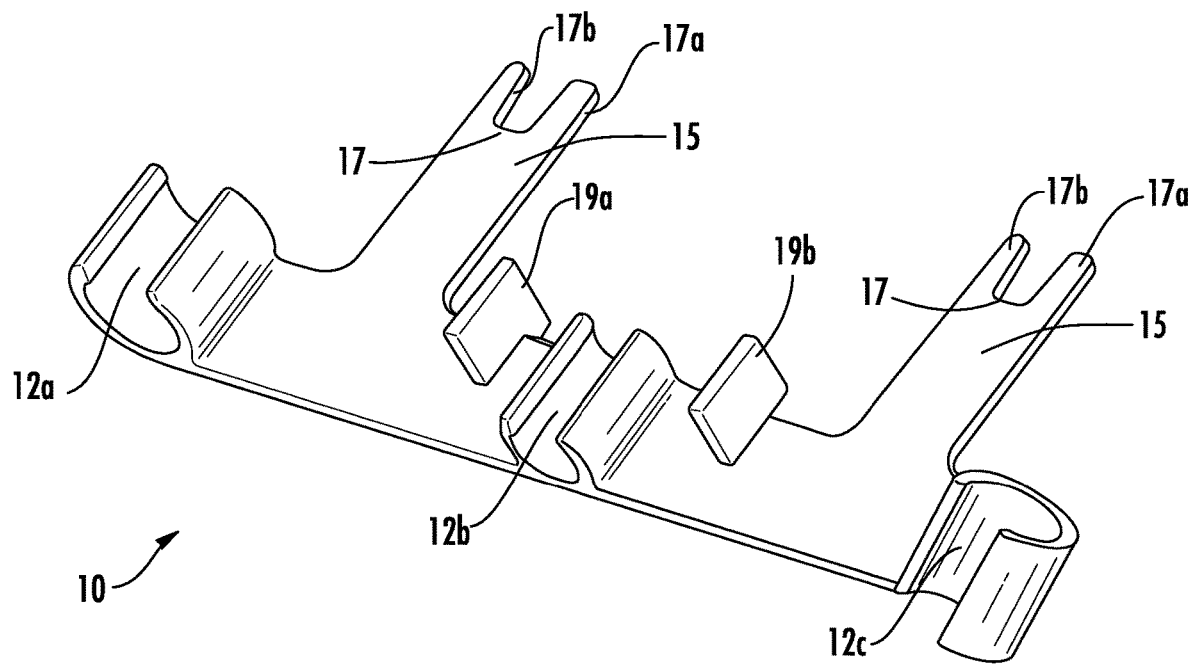
FIG. 10 is a front perspective view of a trocar packaging clip having three holding structures, one for a trocar obturator and two for trocar cannulas, in accordance with an embodiment of the present invention.

In another embodiment, shown for example in FIG. 10, the packaging clip 10 may have more than two holding structures, 12a, 12b, 12c, to hold an obturator and two cannula, for example. Other combinations are possible to accommodate different numbers and combinations of devices.

In the embodiment shown in FIGS. 3 to 6, the packaging clip 10 further includes a finger 15 for preventing the trocar cannula 30 from substantially rotating. The finger 15 includes a notch 17, defined by notch sides 17a and 17b, that the stopcock lever 23 of the trocar cannula—30 is positioned in. This notch 17 of the finger 15 prevents the rotation of the stopcock lever 23 so that the device is presented to a surgeon ready to use with a valve in a predetermined position, e.g., open or closed. This arrangement of the finger 15, having the notch 17 positioned as shown in FIGS. 3 to 6, is particularly well-suited for trocar cannula arrangements in which the stopcock valve lever 23 is configured to rotate about an axis that is parallel to a longitudinal axis of the trocar cannula 30.

Figure 7:
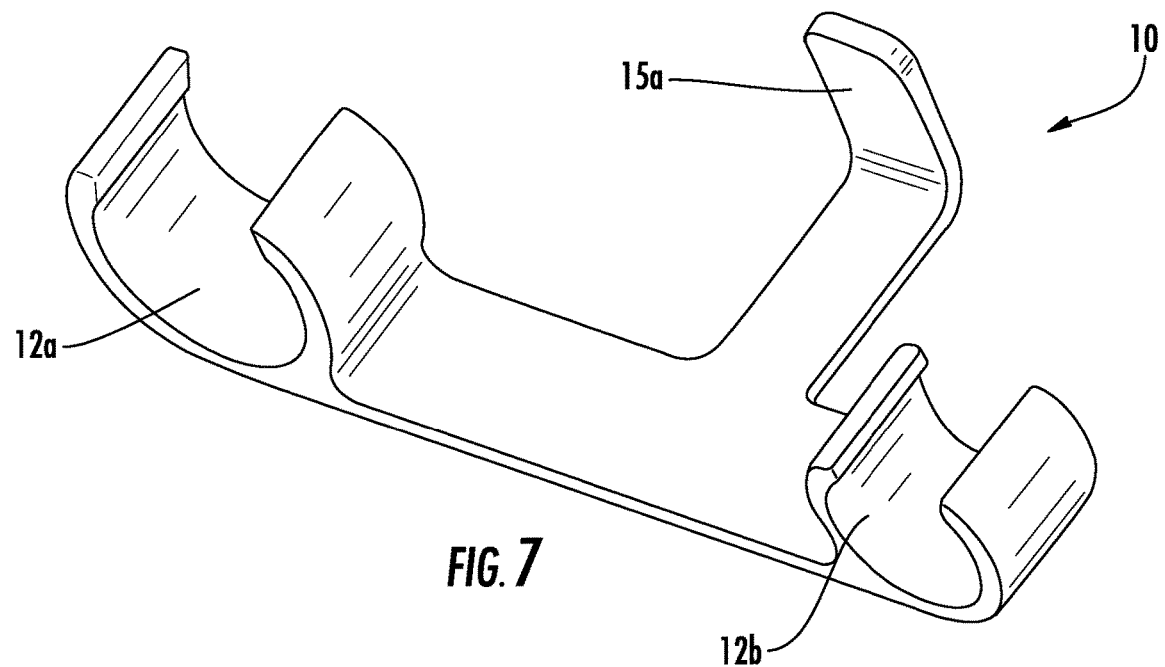
FIG. 7 is perspective front view of a trocar packaging clip, in accordance with another embodiment of the present invention.
Figure 8:
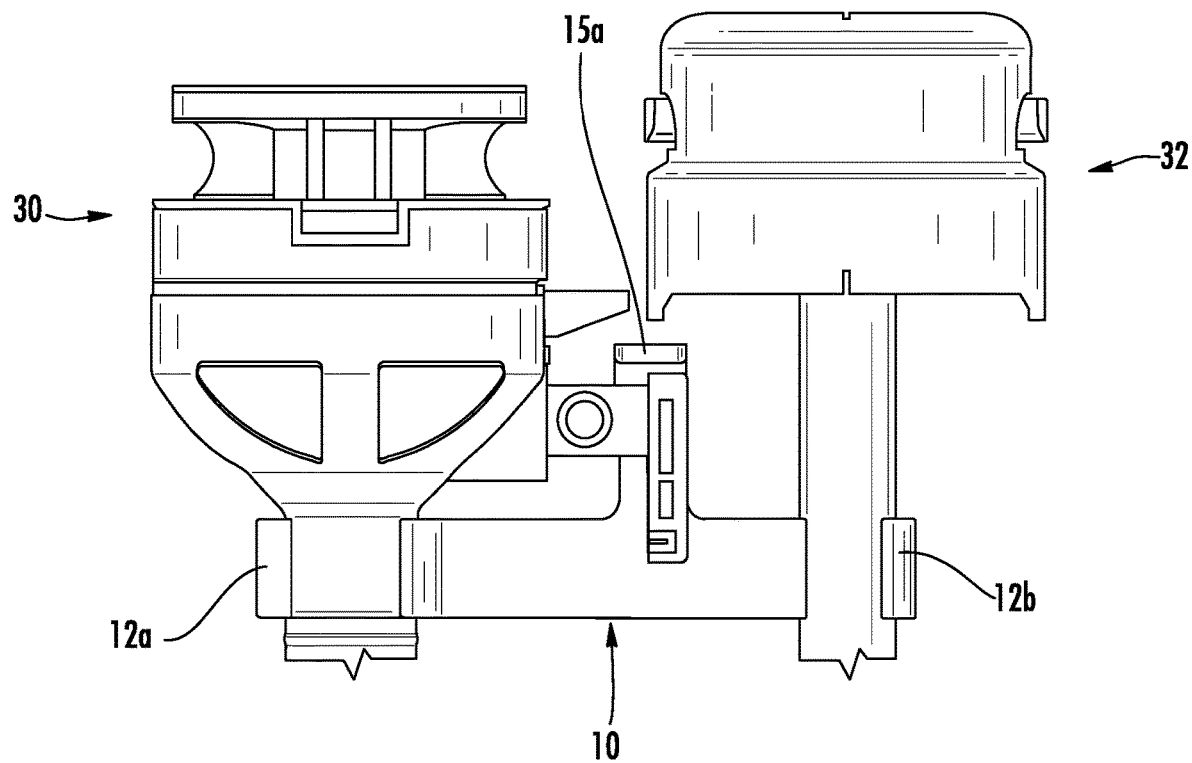
FIG. 8 is a front view of the trocar packaging clip of FIG. 7 having a trocar cannula and trocar obturator attached thereto.
Figure 9:
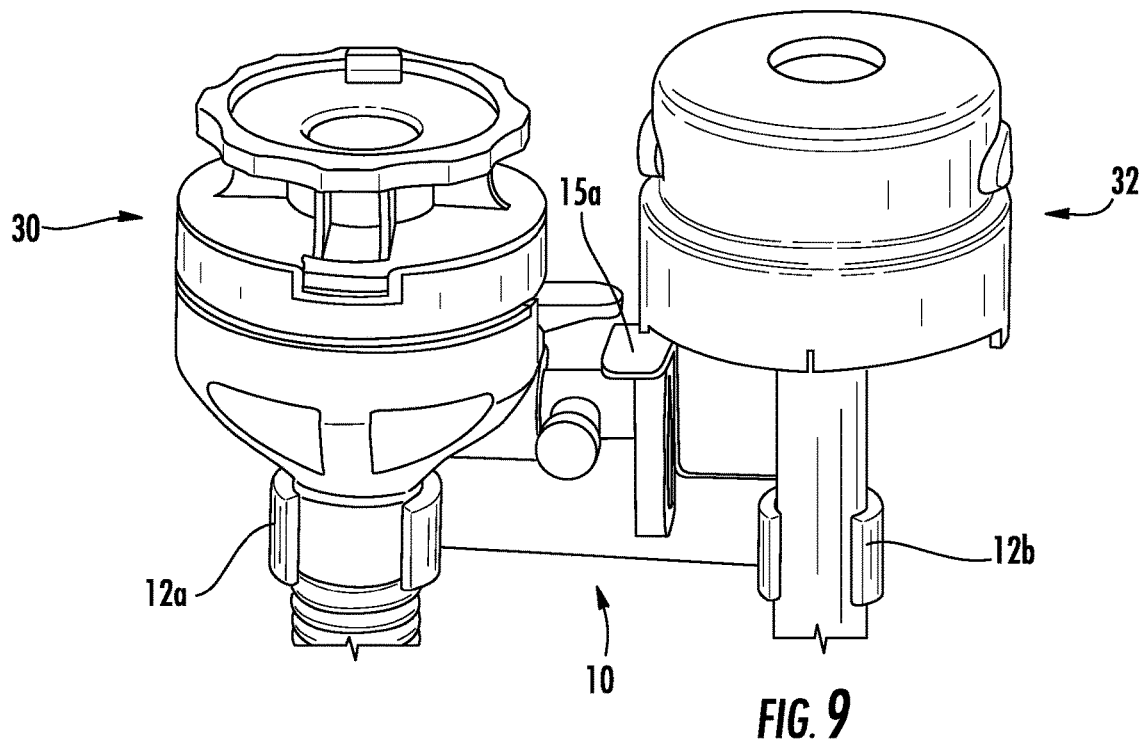
FIG. 9 is a front perspective view of the trocar packaging clip of FIG. 7 having a trocar cannula and trocar obturator attached thereto.

FIGS. 7 to 9 show another e embodiment of the packaging clip 10 where the finger 15a, for example, extend proximally and then perpendicularly over the stopcock lever 23 of the trocar cannula to prevent inadvertent rotation of the stopcock lever 23. This arrangement of the finger 15a, extending proximally and then perpendicularly over the stopcock lever 23 of the trocar cannula, is particularly well-suited for trocar cannula arrangements in which the stopcock valve lever 23 is configured to rotate about an axis that is perpendicular to a longitudinal axis of the trocar cannula 30. Like the embodiment shown in FIGS. 3 to 6, this arrangement protects the sterile barrier of the packaging from the stopcock lever 23, as well as ensures that a surgeon is presented with the device in a configuration that is ready to use.

Referring back to FIGS. 3 to 6, the packaging clip 10 may also include two guards 19a and 19b that may be vertical and that are affixed to the packaging clip 10 nearby the outer perimeter of the trocar obturator 32 for protecting a latch feat not shown) of the trocar obturator 32. The guards 19a and 19b may be located on the same side of the packaging clip 10 as the holding structures 12a and 12b are located. The guards 19a and 19b can be formed, e.g., molded integrally, with the packaging clip 10, or may be affixed to the packaging clip 10 separately after the packaging clip 10 is formed.

In an embodiment, the packaging clip 10 may be yellow in color, since yellow is typically known to indicate a disposable, e.g., non-operational, component to the operating personnel. Other colors may also be used.

An advantage of the present invention over the prior art is that the packaging clip prevents damage of the sterile barrier by preventing rotation of the components of the trocar assembly during shipping, transportation and storage. Moreover, the packaging clip is easy to use for surgeons and not expensive to manufacture.

While the invention has been described in detail herein in accordance with certain preferred embodiments thereof, many modifications and changes therein may be effected by those skilled in the art. Accordingly, it is intended by the appended claims to cover all such modifications and changes as fall within the spirit and scope of the invention.

What is claimed:

1. A trocar assembly including a packaging device, comprising:
   a trocar obturator;
   a cannula having a stopcock lever;
   a clip defining a first longitudinal axis along a length thereof, the clip configured to detachably secure the trocar obturator and the cannula thereto such that the trocar obturator and the cannula are substantially parallel with respect to the first longitudinal axis of the clip, the clip including a finger including a thickness and a length orthogonal to the thickness and greater than the thickness, the length defining a second longitudinal axis substantially parallel with the first longitudinal axis of the clip, the finger including an engaging portion and opposing guides defining a notch therebetween, the finger defining an opening axially spaced apart from the engaging portion along the second longitudinal axis, the notch having a general concavity along the length of the finger, a portion of the stopcock lever of the cannula extending through the notch to inhibit rotation of the stopcock lever.

2. The trocar assembly of claim 1, wherein the clip includes at least one holding structure that defines a c-shape.

3. The trocar assembly of claim 2, wherein the at least one holding structure defines a gap dimensioned to receive at least a portion of the trocar obturator or the cannula.

4. The trocar assembly of claim 1, wherein the clip further comprises at least one holding structure configured to securely retain the trocar obturator or cannula.

5. The trocar assembly of claim 1, wherein the clip further comprises at least one guard.

6. The trocar assembly of claim 1, wherein the clip is configured to detachably secure respective proximal portions of the trocar obturator and the cannula thereto.

7. The trocar assembly of claim 1, wherein the length of the finger of the clip extends along the second longitudinal axis such that a proximal-most end of the finger is proximal of a proximal portion of the cannula.

8. The trocar assembly of claim 1, wherein the portion of the stopcock lever of the cannula that extends through the notch inhibits rotation of the stopcock lever about an axis parallel to the second longitudinal axis.

9. The trocar assembly of claim 1, wherein the opening of the finger leads into the notch.

* * * * *